US012622582B2

(12) United States Patent
Boutinon

(10) Patent No.: US 12,622,582 B2
(45) Date of Patent: May 12, 2026

(54) METHOD AND DEVICE FOR DETERMINING A REFRACTION FEATURE OF AN EYE OF A SUBJECT USING AN IMAGE-CAPTURE DEVICE

(71) Applicant: Essilor International, Charenton-le-Pont (FR)

(72) Inventor: Stephane Boutinon, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 778 days.

(21) Appl. No.: 17/618,262

(22) PCT Filed: Jun. 11, 2020

(86) PCT No.: PCT/EP2020/066211
§ 371 (c)(1),
(2) Date: Dec. 10, 2021

(87) PCT Pub. No.: WO2020/249679
PCT Pub. Date: Dec. 17, 2020

(65) Prior Publication Data
US 2022/0301294 A1 Sep. 22, 2022

(30) Foreign Application Priority Data

Jun. 13, 2019 (EP) .................................... 19305754

(51) Int. Cl.
*A61B 3/103* (2006.01)
*A61B 3/14* (2006.01)
(Continued)

(52) U.S. Cl.
CPC ................ *A61B 3/103* (2013.01); *A61B 3/14* (2013.01); *G06T 5/73* (2024.01); *G06V 10/454* (2022.01);
(Continued)

(58) Field of Classification Search
CPC ..................................................... A61B 3/103
See application file for complete search history.

(56) References Cited

U.S. PATENT DOCUMENTS 7,261,412 B2 * 8/2007 Somani ..................... A61F 9/00
606/4
7,654,674 B2 * 2/2010 Hegels ................. A61B 3/1015
351/205
(Continued)

FOREIGN PATENT DOCUMENTS

JP      2001-120504 A    5/2001
WO      WO 02/30273 A1   4/2002
WO      WO 2007/005261 A2  1/2007

OTHER PUBLICATIONS

Vasyl V. Molebny, Igor H. Chyzh, Vyacheslav M. Sokurenko, Ioannis G. Pallikaris, Leonidas P. Naoumidis, "Eye aberration analysis with Zernike polynomials," Proc. SPIE 3246, Ophthalmic Technologies VIII, (Jun. 1, 1998); https://doi.org/10.1117/12. 309427 (Year: 1998).*

(Continued)

*Primary Examiner* — Zachary W Wilkes
(74) *Attorney, Agent, or Firm* — Oblon, McClelland, Maier & Neustadt, L.L.P.

(57) ABSTRACT

A system and method for determining a refraction feature of an eye of a subject using an image-capture device, the method including acquiring at least one picture of the retina of the eye of the subject, and determining the refraction feature based on a blur level of the acquired picture of the retina.

14 Claims, 2 Drawing Sheets

(51) Int. Cl.

| | |
|---|---|
| *G06T 5/73* | (2024.01) |
| *G06V 10/44* | (2022.01) |
| *G06V 10/82* | (2022.01) |
| *G06V 40/18* | (2022.01) |
| *G06V 40/19* | (2022.01) |

(52) U.S. Cl.
CPC .............. *G06V 10/82* (2022.01); *G06V 40/19* (2022.01); *G06V 40/193* (2022.01); *G06T 2207/20084* (2013.01); *G06V 40/18* (2022.01)

(56) References Cited

U.S. PATENT DOCUMENTS

| | | | | |
|---|---|---|---|---|
| 7,997,731 | B2 * | 8/2011 | Dai | A61B 3/14 351/208 |
| 10,548,473 | B2 * | 2/2020 | Escalier | G02B 30/27 |
| 11,659,989 | B2 * | 5/2023 | Marin | A61B 3/0058 351/239 |
| 11,944,383 | B2 * | 4/2024 | Suchkov | A61B 3/0008 |
| 2002/0140902 | A1 | 10/2002 | Guirao et al. | |
| 2007/0002274 | A1 * | 1/2007 | Somani | A61F 2/16 351/159.75 |
| 2008/0246916 | A1 * | 10/2008 | Hegels | A61B 3/1015 351/205 |
| 2010/0103376 | A1 * | 4/2010 | Dai | A61B 3/14 351/246 |
| 2018/0116500 | A1 * | 5/2018 | Escalier | A61B 3/02 |
| 2020/0069174 | A1 * | 3/2020 | Marin | A61B 3/032 |
| 2023/0380681 | A1 * | 11/2023 | Suchkov | A61B 3/0008 |

OTHER PUBLICATIONS

Lakshminarayanan, Vasudevan, and L. Srinivasa Varadharajan. "Chapter 14: Zernike Polynomials." Special Functions for Optical Science and Engineering, SPIE, Bellingham, WA, 2015, pp. 321-338. (Year: 2015).*

International Search Report issued on Sep. 4, 2020 in PCT/EP2020/066211 filed Jun. 11, 2020, 4 pages.

Lian, J., et al., "Deblurring retinal optical coherence tomography via a convolutional neural network with anisotropic and double convolution layer", IET Computer Vision, The Institution of Engineering and Technology, vol. 12, No. 6, 2018, pp. 900-907.

Chan, T.F., et al., "Total Variation Blind Deconvolution", Transactions on Image Processing, vol. 7, No. 3, 1998, XP-000738213, pp. 370-375.

Uvais, Q., et al., "Blind Deconvolution for Retinal Image Enhancement", Conference on Biomedical Engineering & Sciences, 2010, XP031936712, pp. 20-25.

Pamplona, V., et al., "NETRA: Interactive Display for Estimating Refractive Errors and Focal Range", ACM Transactions on Graphics, vol. 29, No. 4, 2010, XP058157964, pp. 1-8.

Pertuz, S., et al., "Analysis of focus measure operators for shape-from-focus", Pattern Recognition, vol. 46, 2013, pp. 1415-1432.

Japanese Office Action mailed Mar. 18, 2024 in corresponding Japanese Patent Application No. 2021-573910 (with English translation), 13 pages.

* cited by examiner

METHOD AND DEVICE FOR DETERMINING A REFRACTION FEATURE OF AN EYE OF A SUBJECT USING AN IMAGE-CAPTURE DEVICE

TECHNICAL FIELD OF THE INVENTION

The invention relates to a method and a system for determining a refraction feature of an eye of a subject.

BACKGROUND INFORMATION AND PRIOR ART

Numerous documents describe devices and methods for determining such a refraction feature.

In particular, methods of autorefraction are known for determining objective values of the refraction of a subject. These methods are complex and sometimes time-consuming. They usually imply the use of large and expensive devices that need a qualified person to be handled.

In particular, they require the use of a specific instrument having a camera and multiple light sources placed in a same plane.

The access to these methods of autorefraction is therefore limited and a large part of the world population does not benefit from them.

SUMMARY OF THE INVENTION

Therefore one object of the invention is to provide a new method for determining a refraction feature of an eye of a subject that would be simplified in that it would not require the use of specific material or the intervention of qualified people.

More precisely, the invention consists in a method for determining a refraction feature of an eye of a subject using an image-capture device. The method comprises the following steps:

acquiring at least one picture of the retina of the eye of the subject, and determining said refraction feature based on a blur level of said acquired picture of the retina, a blur level of a picture being determined using a value of a point spread function associated with said picture, said refraction feature being determined by calculating a modified picture having a reduced blur level compared to an initial blur level of said acquired picture of the retina.

Such a method may be implemented by the subject himself, and carried on using only a smartphone, or a tablet computer, with no added optical components or an augmented reality display. It is therefore accessible to a wide range of population including some that are excluded from the access to existing methods.

Other advantageous features of the method are the following ones:

said refraction feature is determined by using a model relating said blur level of the acquired picture of the retina to the refraction feature;

the method further comprises a step of acquiring at least a picture of a pupil of the eye of the subject, the step of determining said refraction feature depending on a pupil diameter determined from said picture of the pupil;

the blur level is determined using a convolutional neural network;

the neural network is trained using a dataset of couples of images, each couple of images being associated with a specific refraction feature;

the method further comprises a step of determining a value of a point spread function associated with the acquired picture of the retina by using the training of the neural network with the dataset of couples of images;

the method further comprises a step of determining the refraction feature associated with the acquired picture of the retina by using the training of the neural network with the dataset of couples of images;

the modified picture is calculated using a blind deconvolution method of the acquired picture of the retina;

the blind deconvolution method is based on a dataset of values of the point spread function, each value of the point spread function being associated with a specific refraction feature;

the modified picture is determined selecting an optimal value of the point spread function among said dataset of values of the point spread function, the optimal value of the point spread function corresponding to an improved contrast level in the modified picture compared to an initial contrast level of the acquired picture of the retina;

the picture of the retina is acquired with a focus distance at infinity;

the distance between the eye of the subject and the image-capture device is higher than 20 mm; and the method further comprises a step of acquiring another picture of the retina of the eye of the subject, said another picture is acquired at another focus distance comprised between the one of said acquired picture of the retina and the one of said picture of the pupil of the eye, said refraction feature also depending on said another picture of the retina, said another acquired picture being suitable for determining a sign of the refraction feature, the sign of the refraction feature being determined comparing the blur level between said another acquired picture of the retina and said acquired picture of the retina.

The invention also comprises a system for determining a refraction feature of an eye of a subject comprising:

an image-capture device suitable for acquiring at least one picture of the retina of the eye of the subject, and a data processor suitable for determining said refraction feature based on a blur level of said acquired picture of the retina, a blur level of a picture being determined using a value of a point spread function associated with said picture, said refraction feature being determined by calculating a modified picture having a reduced blur level compared to an initial blur level of said acquired picture of the retina.

The system further comprises a housing suitable for containing said image-capture device and said data processor.

The system further comprises a housing suitable for containing said image-capture device, said housing also comprising an electronic entity suitable for sending said acquired picture of the retina to the data processor and for receiving said refraction feature from the data processor.

The system further comprises a light source suitable for illuminating a pupil of the eye of the subject.

DETAILED DESCRIPTION OF EXAMPLE(S)

The following description, given with regard to the appended drawings, which are given by way of non-limiting examples, will allow what the invention consists of and how it can be carried out to be understood.

In the appended drawings:

FIG. 3 shows a first exemplary flowchart corresponding to a method for determining a refraction feature of an eye of a subject according to the invention;

FIG. 5 shows a second exemplary flowchart corresponding to the method for determining a refraction feature of an eye of a subject according to the invention.

Figure 1:
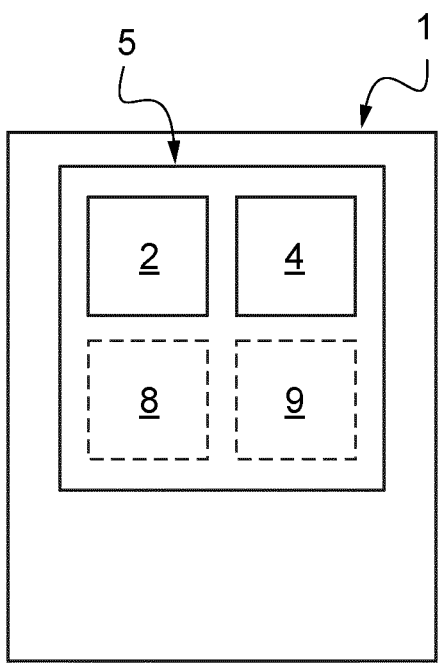
FIG. 1 shows an exemplary system adapted to determine a refraction feature of an eye of a subject according to the invention.
Figure 2:
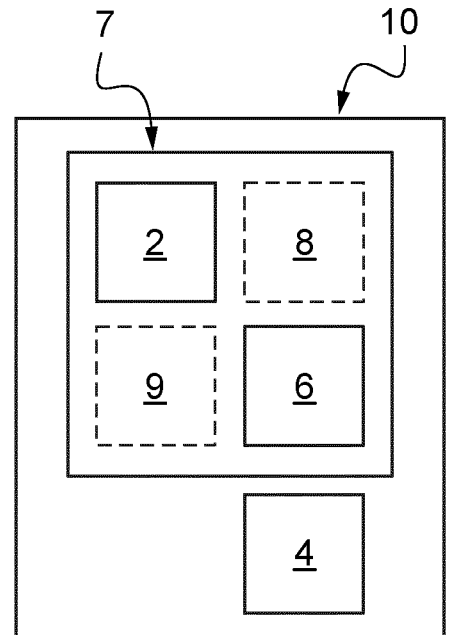
FIG. 2 shows another exemplary system adapted to determine a refraction feature of an eye of a subject according to the invention.
Figure 4:
FIG. 4 is a schematic representation of a configuration in which a system determines a refraction feature of the eye of the subject.

FIGS. 1 and 2 show an exemplary system 1, 10 adapted to determine a refraction feature of an eye 13 of a subject 12 (FIG. 4). In this specification, the refraction features that can be determined comprise the spherical power Sph of a refractive error of the eye of the subject, a cylindrical power C of this refractive error and an orientation θ of the axis of the corresponding cylinder.

In the following, the elements that are shared by both examples of the system 1, 10 have the same references and are described only once.

The system 1, 10 comprises an image-capture device 2 and a data processor 4. Optionally, the system 1, 10 comprises a light source 8.

The image-capture device 2 is a small, general purpose digital camera. The image-capture device 2 is suitable for acquiring at least one picture of the retina of the eye 13 of the subject 12.

The image-capture device 2 is for example located on a face of the system 1, 10 that is oriented in the direction of the subject 12. The image-capture device 2 generally comprises a lens for example defined by an optical axis. The image-capture device 2 is for example a camera included in the system 1, 10. The image-capture device 2 comprises for example a motorized focus device (not represented) that allows the modification of the focus distance while taking pictures.

The optional light source 8 comprises for example one or several LEDs (for "Light Emitting Diodes") or a small electric arc lamp. The light source 8 is suitable for illuminating a pupil of the eye 13 of the subject 12.

The optional light source 8 is located close to the image-capture device 2, in particular close to the optical axis of the lens of said image-capture device 2. In the case of a camera, the optional light source 8 can be a built-in flash light comprised in it.

Preferably, the light source 8 uses near infrared light to avoid pupillary reflex and keep a good diameter of the pupil of the eye 13 of the subject 12. As an alternative, the light source 8 can use white light or red wavelength.

The data processor 4 is suitable for determining the refraction feature based on the pictures acquired by the image-capture device 2. The data processor 4 is associated with a memory (not represented). The memory stores instructions that allow the system 1, 10 to implement a method for determining a refraction feature of the eye 13 of the subject 12 as described below when these instructions are executed by the data processor 4.

According to the exemplary system 1 represented in FIG. 1, the system 1 comprises a housing 5. This housing 5 is suitable for containing the image-capture device 2 and the data processor 4. In this case, the housing is for example a portable electronic device such as a smartphone or a tablet computer.

According to the other exemplary system 10 represented in FIG. 2, the system 10 comprises a housing 7. The housing 7 is suitable for containing the image-capture device 2. In this case, the data processor 4 is located outside the housing 7 of the system 10.

Here, the housing 7 also comprises an electronic entity 6. This electronic entity 6 is suitable for sending acquired pictures of the eye 13 of the subject 12 to the data processor 4 and for receiving the refraction feature from the data processor 4 (after its determination). In this case, the housing 7 is for example a portable electronic device such as a basic camera.

As an alternative, the system can comprise an add-on lens 9. The optical axis of this add-on lens 9 is here aligned with the optical axis of the lens of the image-capture device 2. This add-on lens 9 is used to increase the field of the picture acquired by the image-capture device 2.

Figures 3, 5:
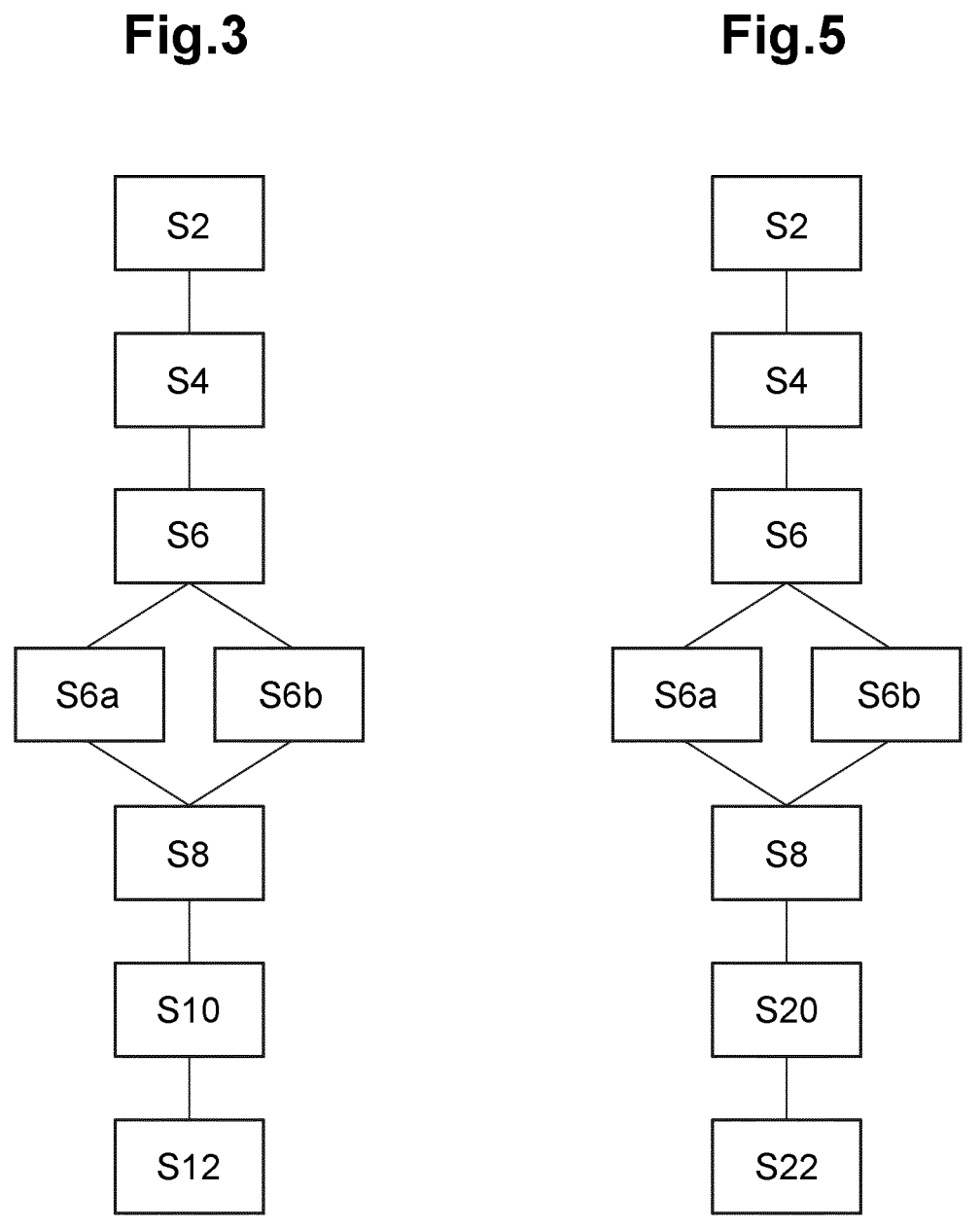

The system 1, 10 shown in FIGS. 1 and 2 and described previously is suitable for executing a method for determining a refraction feature of the eye 13 of the subject 12. FIGS. 3 and 5 show exemplary flowcharts corresponding to a method for determining a refraction feature of the eye 13 of the subject 12 according to the invention.

FIG. 3 describes a schematic representation of the main steps of a first embodiment of the method for determining a refraction feature of the eye 13 of the subject 12. FIG. 5 describes a schematic representation of the main steps of a second embodiment of the method for determining a refraction feature of the eye 13 of the subject 12.

In the following, the steps that are shared by both embodiments have the same references and are described only once.

As represented in FIG. 3, the first embodiment of the method begins with a step S2 in which the subject 12 arranges the housing 5, 7 of the system 1 in front of his face. Particularly, the image-capture device 2 is directed so that it can acquire directly pictures of the eye 13 (retina and pupil) of the subject 12. This configuration is shown in FIG. 4. In practice, the housing 5, 7 of the system 1 can be held on by the subject 12 or by a support (non represented).

In practice, the image-capture device 2 is located close to the eye 13 of the subject 12. The distance D between the eye 13 of the subject 12 and the image-capture device 2 is typically higher than 20 millimeters (mm), for example comprised between 20 mm and 100 mm.

As visible in FIG. 3, the method then comprises a step S4 of illuminating the pupil of the eye 13 of the subject 12. In practice, the illumination is adapted for avoiding a small diameter of the pupil. Preferably, the illumination comes from a low light from the light source 8 or an indoor lighting.

The method continues with a step S6 of acquiring at least one picture of the eye 13 of the subject 12 which was illuminated at the previous step S4. To reduce the accommodation of the eye 13, the subject 12 is looking far ahead during this step.

During this step S6, at a substep S6a, at least one picture of the retina of the eye 13 of the subject 12 is acquired. Preferably here, two different pictures of the retina of the eye 13 of the subject 12 are acquired.

The first picture of the retina, also called "the reference picture of the retina" in the following, is acquired with a focus distance at infinity. In order to acquire this reference picture of the retina, the image-capture device 2 is located at a large focus distance from the eye 13 of the subject 12, for example at a focus distance higher than 4 m.

The second picture of the retina of the eye 13 of the subject 12 is acquired at another focus distance comprised between the one of the acquired reference picture of the retina and the image-capture device 2.

The step S6 also comprises a substep S6b of acquiring at least a picture of the pupil of the eye 13 of the subject 12. The picture of the pupil of the eye 13 of the subject 12 is acquired at a focus distance lower than the focus distances of acquisition of the pictures of the retina of the eye 13.

As an example, the motorized focus device included in the image-capture device 2 can be used to modify the focus distance in order to acquire the picture of the pupil, the reference and the second pictures of the retina of the eye 13.

Here, the sequence of the three pictures (combining substeps S6a and S6b) is taken in a short time interval, for example lower than 0.5 seconds (s). This short time interval ensures the same conditions for the three pictures and thus improves the precision of the further analysis.

Referring to the different focus distances of acquisition of the pictures previously described, in practice for this step S6, it is possible to position the motorized focus device at a first focus distance, for example the closest one or the farthest one, and acquire the picture, then move the motorized focus device to a second focus distance (for example the middle focus distance), and acquire another picture and finally move again the motorized focus device to the last focus distance, and acquire the last picture (without exceeding the time limit).

As represented in FIG. 3, the method then comprises the step S8. During this step, the acquired pictures are transmitted to the data processor 4 in order to be analysed.

Here, the analysis (and thus the determination of the refraction feature) is based on a blur level of the reference picture of the retina.

In this specification, the expression "blur level" of a picture is associated with a measure of a degree of focus of an image for example as introduced in the article "*Analysis of focus measure operators in shape-from-focus*" by S. Petruz, D Puig, M. A. Garcia (Pattern Recognition, 46, 2013, 1415-1432). A high degree of focus relates to a low blur level (the picture is thus sharp).

As an alternative, a contrast level of the picture can be associated with the blur level. The contrast level is for example determined using a Fourier transform analysis. A high contrast level relates to a low blur level (the picture is thus sharp). As an example, the contrast level of the picture can be determined pixel by pixel.

Advantageously thanks to the invention, the determination of the blur level makes possible to derive the refraction feature such as the spherical power Sph of a refractive error of the eye 13 of the subject 12.

In practice, the blur level of a picture is determined using a value of a point spread function (also know as PSF) associated with this picture. Indeed, the surface (also called "spread") of the point spread function is directly linked to the blur level as the point spread function depends on the refractive errors of the eye. An extended point spread function means that the associated picture is very blurry whereas a narrow point spread function is associated with a sharp image.

However, the refraction feature cannot be easily and directly derived from the value of the point spread function in a classic way. A plurality of values of the point spread functions is memorised in the memory of the data processor 4. This plurality of values of the point spread functions is for example determined theoretically from arbitrary refraction features as described in the following.

The classical sphero-cylindrical features (Sphere S, Cylinder C, Orientation θ) are usually represented by a triplet of orthogonal values (Sph, J0, J45) defined as a spherical power $$Sph = S + \frac{C}{2}$$

and two Jackson crossed cylinder lenses one at axis 0° with a power J0=C×cos(2θ) and the other at axis 45° with a power J45=C×sin(2θ), as the astigmatism decomposition of the polar form of astigmatism (C, θ).

This triplet of orthogonal values (Sph, J0, J45) is then used to determine the Zernike coefficients:

$$c_2^{-2} = \frac{R^2 \times J45}{4\sqrt{6}}; \, c_2^2 = \frac{R^2 \times J0}{4\sqrt{6}}; \, c_2^0 = -\frac{R^2 \times Sph}{4\sqrt{3}},$$

with R the pupil ray. Finally, from these Zernike coefficients, an expression of the wavefront W(ρ, θ) can be derived as follows:

$$W(\rho, \theta) = c_2^{-2} \sqrt{6} \, \rho^2 \, \sin(2\theta) + c_2^0 \sqrt{3} \, (2\rho^2 - 1) + c_2^2 \sqrt{6} \, \rho^2 \, \cos(2\theta).$$

The value of the point spread function is then theoretical calculated directly from the wavefront by determining the Fourier transform and the squared modulus. A plurality of theoretical values of the point spread functions is then determined before the execution of the method according to the invention.

A measured value of the point spread function of the reference picture of the retina of the eye 13 of the subject 12 is here determined at step S10, using the determined plurality of theoretical values of the point spread function and corresponding refraction features.

Advantageously, according to the first embodiment of the method represented in FIG. 3, the measured value of the point spread function associated to the reference picture of the retina is determined using a convolutional neural network.

As it is done classically, the convolutional neural network is trained before using. Here, the convolutional neural network is trained before the execution of the method according to the invention.

The convolutional neural network is trained using a dataset of couples of images for a given pupil diameter. Each couple of images comprises a blurred image of the retina of an eye of the subject and an associated unblurred image. In practice, the unblurred image corresponds to a modified picture having a reduced blur level compared to an initial blur level of the associated blurred image. In practice, the modified picture presents a better degree of focus or a better contrast level.

Each couple of images is associated with a specific value of the point spread function and thus with a specific refraction feature. The different couples of images of the retina are simulated with a model, thus allowing the generation of a large number of couples of images. For the training part, blurred images are generated using unblurred images that are convolved with associated point spread functions.

Here, the convolutional neural network is for example trained using as an input data the blurred image of the couple of images and as an output data the associated value of the point spread function.

At the step S10, the reference picture of the retina of the eye 13 of the subject 12 is introduced as the input of the convolutional neural network. Thanks to the training previously performed, the measured value of the point spread function associated to this reference picture of the retina is obtained at the output of the convolutional neural network.

Knowing the pupil diameter of the subject 12 thanks to the picture of the pupil of the eye 13 of the subject 12 acquired at the step S6b, it is then possible to extract the refraction feature, for example by using the Zernike coefficients. In practice, this step S10 comprises a step of minimizing the difference between the measured value of the point spread function and one of the plurality of theoretical values of the point spread functions memorised in the memory of the data processor 4. The minimum difference allows determining the corresponding theoretical value of the point spread function and thus the associated refraction feature.

As an alternative, the convolutional neural network can be trained using as the input data the blurred image of the couple of images and as the output data the associated refraction feature. At the step S10, by introducing the reference picture of the retina of the eye 13 of the subject 12 in the convolutional neural network, the refraction feature is directly obtained at the output of the convolutional neural network.

As another alternative, the convolutional neural network can be trained using as the input the blurred image of the couple of images and as the output the unblurred image of the couple. In this case, by introducing the reference picture of the retina in the convolutional neural network, an associated modified picture having a reduced blur level compared to the initial blur level of the reference picture of the retina is obtained at the output of the convolutional neural network. As, by definition, the reference picture of the retina of the eye 13 of the subject 12 is determined by the deconvolution of the modified picture and the associated value of the point spread function, this value can be derived from both pictures using traditional deconvolution methods. It is then possible to extract the refraction feature using the pupil diameter, for example by using the Zernike coefficients as described previously.

Finally, at the step S12, the refraction feature is clarified using the second acquired picture of the retina of the eye 13 of the subject 12. In particular, this second picture of the retina is suitable for determining a sign of the refraction feature and thus the sign of the ametropia (in order to identify a myopic eye or a hyperopic eye). As the value of the point spread function is the same for both positive and negative ametropic parameters, the refractive error is fully identified thanks to this second picture of the retina.

The sign of the refraction feature is determined comparing the blur level, based for example on the contrast level, between the second picture of the retina and the reference picture of the retina. If the blur level of the second picture of the retina is higher than the one of the reference picture of the retina, a myopic eye is identified. If the blur level of the second picture of the retina is lower than the one of the reference picture, the refractive error is associated with a hyperopic eye.

As another example, if the housing 7 is a smartphone, the focus distance is ranging between 70 mm and infinity. As the image of the retina is formed at a focus distance equal to the opposite of the inverse of the spherical power, this parameter is positive.

FIG. 5 describes a schematic representation of the main steps of a second embodiment of the method for determining a refraction feature of the eye 13 of the subject 12.

As represented in FIG. 5, this second embodiment of the method for determining a refraction feature of the eye 13 of the subject 12 also comprises the steps S2 to S8 previously described.

As previously introduced, here, the analysis (and thus the determination of the refraction feature) is based on the analysis of the blur level of the reference picture of the retina.

Advantageously thanks to the invention, the determination of the blur level makes possible to derive the refraction feature such as the spherical power of a refractive error of the eye 13 of the subject 12.

In this second embodiment of the method, the blur level of the reference picture is determined using a value of the point spread function associated with this picture. The value of the point spread function of the reference picture of the retina of the eye 13 of the subject 12 is thus determined at step S20.

Advantageously, according to the second embodiment of the method represented in FIG. 5, this value of the point spread function of the reference picture of the retina is determined using a blind deconvolution method. This blind deconvolution method is applied to the reference picture of the retina in order to determine simultaneously the modified picture with a reduced blur level compared to the initial one of the reference picture of the retina and the associated value of the point spread function. The blind deconvolution method used here is for example an iterative method such as the Lucy-Richardson deconvolution method or a Bayesian-method deconvolution method. As another example, the blind deconvolution method can be a non-iterative method such as SeDDaRa deconvolution method or a Cepstrum-based method.

Here, the deconvolution method is based on a dataset of values of the point spread function. The different values of the point spread function are calculated for different refraction features for a given pupil diameter. In fact here, each value of the point spread function of the dataset is associated with a specific refraction feature.

The modified picture obtained at the output of the method is derived by determining an optimal value of the point spread function among the dataset of values of the point spread function. In other words, the modified picture is obtained by optimising the value of the point spread function among the dataset of values of the point spread function.

The optimal value of the point spread function is here determined considering the deconvolved picture with an improved contrast level compared to an initial contrast level of the reference picture of the retina. This picture, also called "modified picture", is thus sharper than the reference picture of the retina (its blur level is thus lower).

Once, the value of the point spread function is determined and knowing the pupil diameter of the subject 12 thanks to the picture of the pupil of the eye 13 of the subject 12 acquired at the step S6b, it is possible to extract the refraction feature, for example by using the Zernike coefficients as described previously.

Finally, at the step S22 (similar to the previously described step S12), the refraction feature is clarified using the second acquired picture of the retina of the eye 13 of the subject 12 in order to determine the sign of the refraction feature and thus the sign of the ametropia (in order to identify a myopic eye or a hyperopic eye).

The present invention has been described in connection with what are considered the most practical and preferred embodiments. It is understood that this invention is not limited to the disclosed embodiments but is intended to cover various arrangements included within the spirit and scope of the broadest interpretation and equivalent arrangement.

The invention claimed is:

1. A method for determining a refraction feature of an eye of a subject using an image-capture device, said method comprising:

acquiring at least one picture of a retina of the eye of the subject; and determining said refraction feature based on a blur level of said acquired picture of the retina, the blur level of a picture being determined using a value of a point spread function associated with said acquired picture, said refraction feature being determined by:

calculating a modified picture having a reduced blur level compared to an initial blur level of said acquired picture of the retina, said value of a point spread function associated with said acquired picture is derived from the acquired picture and the modified picture using a deconvolution method, and identifying one theoretical value of a point spread function of a plurality of theoretical values of the point spread function which has a minimal difference between said value of the point spread function associated with said acquired picture and the one theoretical value of the point spread function of the plurality of theoretical values of the point spread function, to determine the corresponding theoretical value of the point spread function and the refraction feature associated with the corresponding theoretical value of the point spread function and thus the refraction feature of the eye of the subject, or optimizing the value of the point spread function associated with said acquired picture among the plurality of theoretical values of the point spread function to determine the corresponding theoretical value of the point spread function and the refraction feature associated with the corresponding theoretical value of the point spread function and thus the refraction feature of the eye of the subject, an optimal value of the point spread function being determined considering the modified picture with a different contrast level compared to an initial contrast level of the acquired picture, each theoretical value of the point spread function of the plurality of theoretical values of the point spread function being determined theoretically from an arbitrary refraction feature which is thus associated with said theoretical value of the point spread function, said arbitrary refraction feature being used to determine Zernike coefficients and derive an expression of a wavefront to calculate said theoretical value of the point spread function of the plurality of theoretical values of the point spread function, the plurality of theoretical values of the point spread function being determined before an execution of the method for determining a refraction feature.

2. The method according to claim 1, wherein said refraction feature is determined by using a model relating said blur level of the acquired picture of the retina to the refraction feature.

3. The method according to claim 1, further comprising acquiring at least a picture of a pupil of the eye of the subject, the determining said refraction feature depending on a pupil diameter determined from said picture of the pupil.

4. The method according to claim 3, further acquiring another picture of the retina of the eye of the subject, said another picture is acquired at another focus distance comprised between the one of said acquired picture of the retina and the one of said picture of the pupil of the eye, said refraction feature also depending on said another picture of the retina, said another acquired picture being suitable for determining a sign of the refraction feature, the sign of the refraction feature being determined comparing the blur level between said another acquired picture of the retina and said acquired picture of the retina.

5. The method according to claim 1, wherein the blur level is determined using a convolutional neural network.

6. The method according to claim 5, wherein the convolutional neural network is trained using a dataset of couples of images, each couple of images being associated with a specific refraction feature.

7. The method according to claim 6, further comprising determining a value of a point spread function associated with the acquired picture of the retina by using the training of the convolutional neural network with the dataset of couples of images.

8. The method according to claim 6, further comprising determining the refraction feature associated with the acquired picture of the retina by using the training of the convolutional neural network with the dataset of couples of images.

9. The method according to claim 1, wherein the modified picture is calculated using a blind deconvolution method of the acquired picture of the retina.

10. The method according to claim 9, wherein the blind deconvolution method is based on a dataset of values of the point spread function, each value of the point spread function being associated with a specific refraction feature.

11. The method according to claim 10, wherein the modified picture is determined selecting an optimal value of the point spread function among said dataset of values of the point spread function, the optimal value of the point spread function corresponding to an improved contrast level in the modified picture compared to an initial contrast level of the acquired picture of the retina.

12. The method according to claim 1, wherein the picture of the retina is acquired with an image capture device with a focus distance at infinity.

13. The method according to claim 1, wherein a distance between the eye of the subject and the image-capture device is higher than 20 mm.

14. A system for determining a refraction feature of an eye of a subject comprising:

an image-capture device suitable for acquiring at least one picture of a retina of the eye of the subject; and a data processor suitable for determining said refraction feature based on a blur level of said acquired picture of the retina, a blur level of a picture being determined using a value of a point spread function associated with said acquired picture, said data processor being suitable for determining the refraction feature by:

calculating a modified picture having a reduced blur level compared to an initial blur level of said acquired picture of the retina, said value of a point spread function associated with said acquired picture being derived from the acquired picture and the modified picture using a deconvolution method, and identifying one theoretical value of a point spread function of a plurality of theoretical values of the point spread function which has a minimal difference between said value of the point spread function associated with said acquired picture and the one theoretical value of the point spread function of the plurality of theoretical values of the point spread functions, to determine the corresponding theoretical value of the point spread function and the refraction feature associated with the corresponding theoretical value of the point spread function and thus the refraction feature of the eye of the subject, or optimizing the value of the point spread function associated with said acquired picture among the plurality of theoretical values of the point spread function to determine the corresponding theoretical value of the point spread function and the refraction feature associated with the corresponding theoretical value of the point spread function and thus the refraction feature of the eye of the subject, an optimal value of the point spread function being determined considering the modified picture with a different contrast level compared to an initial contrast level of the acquired picture, said data processor being suitable for determining theoretically each theoretical value of the point spread function of the plurality of theoretical values of the point spread function from an arbitrary refraction feature which is thus associated with said theoretical value of the point spread function, said arbitrary refraction feature being used to determine Zernike coefficients and derive an expression of a wavefront to calculate said theoretical value of the point spread function of the plurality of theoretical values of the point spread function, the plurality of theoretical values of the point spread function being determined before an execution of determining a refraction feature.

* * * * *